(12) United States Patent
Ramani et al.

(10) Patent No.: US 7,041,621 B2
(45) Date of Patent: May 9, 2006

(54) SULFIDED CATALYSTS FOR IMPROVED PERFORMANCE IN HYDROCARBON PROCESSING

(75) Inventors: Sriram Ramani, Ponca City, OK (US); Alfred E. Keller, Ponca City, OK (US); Joe D. Allison, Ponca City, OK (US); Zhen Chen, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 407 days.

(21) Appl. No.: 10/346,427

(22) Filed: Jan. 17, 2003

(65) Prior Publication Data
US 2004/0140245 A1    Jul. 22, 2004

(51) Int. Cl.
*B01J 27/02* (2006.01)

(52) U.S. Cl. ........................ 502/216; 423/651
(58) Field of Classification Search .............. 208/48 R; 252/373; 423/651; 502/216, 219, 220, 221, 502/223, 305–355
See application file for complete search history.

(56) References Cited

U.S. PATENT DOCUMENTS

| | | | |
|---|---|---|---|
| 4,039,429 A | 8/1977 | Van Klinken et al. | 208/50 |
| 4,104,152 A | 8/1978 | Hilfman | 208/112 |
| 4,171,258 A | 10/1979 | Gaspar | 208/114 |
| 4,243,519 A | 1/1981 | Schorfheide | 208/210 |
| 4,256,566 A | 3/1981 | Antos | 208/139 |
| 4,560,804 A | 12/1985 | Yeh et al. | 568/408 |
| 4,737,482 A | 4/1988 | Yeh et al. | 502/220 |
| 4,831,060 A | 5/1989 | Stevens et al. | 518/714 |
| 5,651,878 A | 7/1997 | Sudhakar et al. | 208/143 |
| 5,720,901 A | 2/1998 | De Jong et al. | 252/373 |
| 5,821,191 A | 10/1998 | Lockemeyer | 502/216 |
| 6,075,061 A | 6/2000 | Wittenbrink et al. | 518/715 |
| 6,221,280 B1 | 4/2001 | Anumakonda et al. | 252/372 |
| 6,235,259 B1 | 5/2001 | Ledoux et al. | 423/573.1 |
| 6,409,940 B1 | 6/2002 | Gaffney et al. | 252/373 |

FOREIGN PATENT DOCUMENTS

| | | |
|---|---|---|
| WO | WO 01/34517 A1 | 5/2001 |
| WO | WO 01/36323 A2 | 5/2001 |

OTHER PUBLICATIONS

D. A. Hickman, et al., *Production of Syngas by Direct Catalytic Oxidation of Methane;* Science, vol. 259 (p. 343-346); Jan. 15, 1993.

Nielsen, et al., *Combined TPS, XPS, EXAFS, and No-TPD Study of the Sulfiding of Mo/Al$_2$O$_3$;* Catalysis Letters vol. 73, No. 2-4. 2001 (p. 85-90).

PCT International Search Report for Appln. No. PCT/US04/01563 dated Aug. 10, 2004 (3 p.).

*Primary Examiner*—Colleen P. Cooke
(74) *Attorney, Agent, or Firm*—Conley Rose P.C.

(57) ABSTRACT

A process and catalyst are disclosed for reducing coking in hydrocarbon processing reactions. The preferred embodiments employ a sulfur-containing material such as hydrogen sulfide to reduce catalyst susceptibility to deactivation from carbon deposits formed during processing.

44 Claims, No Drawings

SULFIDED CATALYSTS FOR IMPROVED PERFORMANCE IN HYDROCARBON PROCESSING

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Technical Field of the Invention

The present invention generally relates to catalysts and processes for improving catalyst performance in hydrocarbon processing—e.g., catalytic partial oxidation and catalytic oxidative dehydrogenation. More particularly, the present invention pertains to hydrocarbon processing catalysts and processes in which catalyst life is extended by reducing the formation of carbon deposits ("coking") on the catalyst surface. Even more particularly, the present invention is directed to sulfided catalysts and processes utilizing sulfided catalysts that provide improved catalyst performance and life through reduced catalyst susceptibility to coking.

2. Description of Related Art

There is currently a significant interest in various types of hydrocarbon processing reactions designed to provide high value products from lower value reactants. Such reactions refer to any chemical process using hydrocarbons as a feedstock. One example of a hydrocarbon processing reaction involves the conversion of lower molecular weight gaseous hydrocarbons to higher molecular weight liquid hydrocarbons. Many refineries possess an abundant supply of relatively low value gaseous alkanes—i.e., such as methane and ethane—and few commercially-viable means of converting them to more valuable liquid alkanes. Moreover, vast reserves of methane, the main component of natural gas, are available in many areas of the world. There is great incentive to exploit these natural gas formations because natural gas is predicted to outlast oil reserves by a significant margin; however, most natural gas formations are situated in areas that are geographically remote from population and industrial centers. The costs of compression, transportation, and storage of gaseous hydrocarbons make their use economically unattractive relative to liquid hydrocarbons. Consequently, there is considerable interest in techniques for converting methane and other gaseous hydrocarbons to their heavier liquid hydrocarbon homologs both at refineries and especially at natural gas formations.

The conversion of methane to higher hydrocarbons is typically carried out in two steps. In the first step, methane is partially oxidized to produce a mixture of carbon monoxide and hydrogen known as synthesis gas or syngas. Syngas generation from methane typically takes place by one of three techniques: partial oxidation [1], steam reforming [2], and dry reforming [3]:

$$CH_4 + 1/2 O_2 \rightarrow CO + 2H_2 \qquad [1]$$

$$CH_4 + H_2O \rightarrow CO + 3H_2 \qquad [2]$$

$$CH_4 + CO_2 \rightarrow 2CO + 2H_2 \qquad [3]$$

The syngas product in each case is a mixture of carbon monoxide and molecular hydrogen, generally having a hydrogen to carbon monoxide molar ratio in the range of 1:5 to 5:1, and may contain other gases such as carbon dioxide.

In a second step, the syngas is converted to liquid and solid hydrocarbons using the Fischer-Tropsch process. This method allows the conversion of synthesis gas into liquid hydrocarbon fuels and solid hydrocarbon waxes. In addition, the Fischer-Tropsch process allows the synthesis of alcohols (e.g., methanol) and olefins (e.g., ethylene). High molecular weight waxes provide an ideal feedstock for hydrocracking, a feedstock for conversion to high quality jet fuel and superior high octane value diesel fuel blending components.

Another category of hydrocarbon processing involves the oxidative dehydrogenation of hydrocarbons to give the corresponding alkene, such as the conversion of ethane to ethylene [4]:

$$C_2H_6 + 1/2 O_2 \rightarrow C_2H_4 + H_2O \qquad [4]$$

Unsaturated hydrocarbons, such as the alkenes produced from oxidative dehydrogenation, possess industrial importance owing to their use as feedstocks in producing various commercially useful materials such as detergents, high octane gasolines, pharmaceutical products, plastics, synthetic rubbers and viscosity additives.

Catalysis plays a central role in syngas production, the Fischer-Tropsch reaction, oxidative dehydrogenation and many other hydrocarbon processing techniques. Each of these methods share a common attribute: successful commercial scale operation for catalytic hydrocarbon processing depends upon high hydrocarbon feedstock conversion at high throughput and with high selectivity for the desired reaction products. In each case, the yields and selectivities of catalytic hydrocarbon processing are controlled by several factors. One of the most important of these factors is the choice of catalyst composition, which significantly affects not only the yields and product distributions but also the overall economics of the process. Unfortunately, few catalysts offer both the performance and cost necessary for large-scale industrial use.

From an economic standpoint, desirable conditions for hydrocarbon processing include elevated pressures and temperatures, which translate into increased yields and throughput. Typically, though, hydrocarbon processing at elevated pressures is problematic because of shifts in equilibrium, undesirable secondary reactions and catalyst instability. Furthermore, the high operating temperatures desirable in hydrocarbon processing frequently cause catalyst instability and reduce catalyst life. Consequently, despite a variety of advances, sufficiently stable and long-lived catalysts capable of conversion rates that are attractive for large scale industrial use remain elusive. Accordingly, a continuing need exists for better hydrocarbon processing techniques and catalysts. In such improved processes the catalysts would be stable at high temperatures. They would also retain a high level of hydrocarbon conversion activity and selectivity under conditions of high gas space velocity and elevated pressures for long periods of time on-stream.

One primary cause of shortened catalyst life and reduced stability is coking, which is the formation of carbon deposits ("coke") on the catalyst. Coking causes catalyst deactivation, thereby severely reducing catalyst performance. Substantial effort in this field has been devoted to the development of commercially-viable catalysts with reduced susceptibility to coke formation. Several techniques for minimizing coking have been developed. One technique is to add steam into the feed mixture. This technique, however, entails a number of disadvantages that render it unsatisfactory as a solution to the coking problem. Another technique for reducing coke formation is the use of noble metals, which are generally less susceptible to coking than the more widely used, less expensive, catalysts. Unfortunately, though, the noble metals are scarce and expensive. Furthermore, they are not immune to coking. No satisfactory solution to the coking problem currently exists.

Sulfur is traditionally viewed as a deleterious and undesirable contaminant in hydrocarbon processing reactions. This is true because many of the catalysts that are conventionally used in hydrocarbon processing regimes are believed to be poisoned by the presence of sulfur. Sulfur poisoning is of particular interest because many natural gas formations contain hydrogen sulfide ($H_2S$) in concentrations ranging from trace amounts up to about forty percent by volume. Consequently, catalytic hydrocarbon processing techniques frequently employ a preliminary sulfur removal step.

Despite its reputation as a catalyst poison, sulfur has been employed in catalytic hydrocarbon processing. For example, sulfur-induced catalyst deactivation has been used to improve process selectivity through the selective deactivation of unwanted by-product reactions: because the deactivation of hydrocarbon catalysts with respect to unwanted side reactions can exceed deactivation of the desired process, deliberate catalyst sulfiding can increase catalyst selectivity at the expense of catalyst activity. Under appropriate circumstances, this trade-off of improved selectivity for decreased activity can prove advantageous.

Recently, it has been suggested that sulfur may have some utility in reducing the generation of undesirable nitrogen by-products in natural gas refining. U.S. Pat. No. 5,720,901 ("the '901 patent") describes a process for the catalytic partial oxidation of hydrocarbons in which nitrogen is present in the hydrocarbon feed mixture. According to the '901 patent, an organic or inorganic sulfur-containing compound is present in the feed mixture in a sufficient concentration (i.e., 0.05 to 100 ppm) to reduce the presence of nitrogen by-products, particularly ammonia and hydrogen cyanide, in the products of the catalytic partial oxidation process. It is suggested that hydrocarbon feedstocks used directly from naturally occurring reservoirs in which the sulfur content is significantly above the stated low levels be subjected to a partial sulfur removal treatment before being employed in that process. A sulfur removal step is applied to the product stream if the carbon monoxide and/or hydrogen products of the process are to be utilized in applications that are sensitive to the presence of sulfur, such as Fischer-Tropsch synthesis. Generally speaking, though, sulfur is believed to be a catalyst poison that is deleterious in catalytic hydrocarbon processing.

What is needed is a hydrocarbon processing catalyst and a method of using a hydrocarbon processing catalyst that suppresses the formation of coke and thereby promotes catalyst activity and extends catalyst life. This catalyst and method must be able to achieve a high conversion of the hydrocarbon feedstock with high throughput and product selectivity. Not only is the choice of the catalyst's chemical composition important, the physical structure of the catalyst and catalyst support structures must possess mechanical strength and porosity, in order to function under operating conditions of high pressure and high flow rate of the reactant and product gases.

BRIEF SUMMARY OF PREFERRED EMBODIMENTS

The preferred embodiments of the present invention also include sulfided catalysts that offer improved resistance to coking. The sulfiding step in the preferred embodiments can be performed before, during or after use of the catalyst in a hydrocarbon processing reaction. Preferably, the catalyst is subjected to a sulfiding pretreatment prior to use in a hydrocarbon processing step. The base catalyst can be any appropriate catalyst material with or without a refractory or other appropriate support. Preferably, the catalyst is a noble metal selected from the group consisting of platinum, rhodium, ruthenium, iridium, nickel, palladium, iron, cobalt, rhenium and rubidium, or a combination of any of those metals. More preferably, the catalyst is a mixed-metal catalyst comprising at least one metal selected from the group consisting of rhodium, ruthenium and iridium and at least one metal selected from the group consisting of platinum and palladium. Most preferably, the catalyst is a mixed-metal catalyst comprised of platinum and/or rhodium.

The preferred embodiments of the present invention also include hydrocarbon processing techniques that employ sulfided catalysts to improve reaction yield and economy by increasing catalyst life. Preferably, the hydrocarbon processing techniques are catalytic partial oxidation reactions. More preferably, the catalytic partial oxidation reactions are syngas generation and oxidative alkane dehydrogenation reactions.

DETAILED DESCRIPTION OF PREFERRED EMBODIMENTS

A variety of materials exhibit catalytic activity in various hydrocarbon processing techniques. As an example and without limiting the scope of the invention, synthesis gas catalysts include scandium, titanium, vanadium, chromium, manganese, iron, cobalt, nickel, copper, zirconium, niobium, molybdenum, technetium, ruthenium, rhodium, palladium, silver, hafnium, tantalum, tungsten, rhenium, osmium, iridium, platinum and gold. Preferably the catalytic metal is selected from the group consisting of platinum, rhodium, ruthenium, iridium, nickel, palladium, iron, cobalt, rhenium and rubidium. Platinum and rhodium are especially preferred.

Frequently, catalysts for hydrocarbon processing reactions are composed of two or more metals and are referred to herein as mixed-metal catalysts. A preferred embodiment of the present invention is a mixed-metal catalyst comprising at least one metal selected from the group consisting of rhodium, ruthenium and iridium and at least one metal selected from the group consisting of platinum and palladium. Even more preferably, the mixed metal catalyst comprises platinum and rhodium.

Optionally, the catalyst can include a promoter. Without limiting the scope of the invention, known promoters in hydrocarbon processing reactions include Mg, B, Al, Ln, Ga, Si, Ti, Zr, Hf, Cr, Mn, Co, Mo, W, Sn, Re, Rh, Pd, Ru, Ir, Pt, La, Ce, Sm, Yb, Eu, Pr, Lu, Bi, Sb, In or P, and oxides thereof.

The catalytically active materials and promoters can be used alone or on supports. Preferably, the catalytically active materials and promoters are preferably deposited on supports such as wire gauzes, porous ceramic monoliths, or particles. The term "monolith" refers to any singular piece of material of continuous manufacture such as solid pieces of metal or metal oxide or foam materials or honeycomb structures. Two or more such catalyst monoliths may be stacked in the catalyst zone of the reactor if desired. For example, the catalyst can be structured as, or supported on, a refractory oxide "honeycomb" straight channel extrudate or monolith, made of cordierite or mullite, or other configuration having longitudinal channels or passageways permitting high space velocities with a minimal pressure drop. Such configurations are known in the art and described, for example, in *Structured Catalysts and Reactors*, A. Cybulski and J. A. Moulijn (Eds.), Marcel Dekker, Inc., 1998, p. 599–615 (Ch. 21, X. Xu and J. A. Moulijn, "Transformation of a Structured Carrier into Structured Catalyst"), which is hereby incorporated herein by reference.

Some preferred monolithic supports include partially stabilized zirconia (PSZ) foam (stabilized with Mg, Ca or Y), or foams of $\alpha$-alumina, cordierite, titania, mullite, Zr-stabilized $\alpha$-alumina, or mixtures thereof A preferred laboratory-scale ceramic monolith support is a porous alumina foam with approximately 6,400 channels per square inch (80 pores per linear inch). Preferred foams for use in the preparation of the catalyst include those having from 30 to 150 pores per inch (12 to 60 pores per centimeter). The monolith can be cylindrical overall, with a diameter corresponding to the inside diameter of the reactor tube.

Alternatively, other refractory foam and non-foam monoliths may serve as satisfactory supports. The catalyst precursors, including promoter and lanthanide salts, with or without a ceramic oxide support forming component, may be extruded to prepare a three-dimensional form or structure such as a honeycomb, foam, other suitable tortuous-path structure.

A more preferred catalyst geometry employs distinct or discrete particles. The terms "distinct" or "discrete" particles, as used herein, refer to supports in the form of divided materials such as granules, beads, pills, pellets, cylinders, trilobes, extrudates, spheres or other rounded shapes, or another manufactured configuration. Alternatively, the divided material may be in the form of irregularly shaped particles. Preferably at least a majority (i.e., >50%) of the particles or distinct structures have a maximum characteristic length (i.e., longest dimension) of less than six millimeters, preferably less than three millimeters. Preferably, these particulate-supported catalysts are prepared by impregnating or washcoating the catalytic material and any promoter material onto the refractory particulate support.

Numerous refractory materials have been utilized as supports. Without limiting the scope of the invention, suitable refractory support materials include silicon carbide, boron carbide, tungsten carbide, silicon nitride, boron nitride, tungsten nitride, zirconia, magnesium stabilized zirconia, zirconia stabilized alumina, yttrium stabilized zirconia, calcium stabilized zirconia, alumina, cordierite, titania, silica, magnesia, niobia, vanadia, and the like. Alumina is preferably in the form of alpha-alumina, however the other forms of alumina have also demonstrated satisfactory performance.

The catalyst may be configured in either a fixed bed, fluidized bed, or ebullating bed arrangement. A fixed bed arrangement employs a stationary catalyst and a well-defined reaction volume whereas a fluidized bed utilizes mobile catalyst particles. Conventional fluidized beds include bubbling beds, turbulent fluidized beds, fast fluidized beds, concurrent pneumatic transport beds, and the like. A fluidized bed reactor system has the advantage of allowing continuous removal of catalyst from the reaction zone, with the withdrawn catalyst being replaced by fresh or regenerated catalyst. A disadvantage of fluidized beds is the necessity of downstream separation equipment to recover entrained catalyst particles. Preferably, the catalyst is retained in a fixed bed reaction regime in which the catalyst is retained within a defined reaction zone. Fixed bed reaction techniques are well known and have been described in the literature. Irrespective of catalyst arrangement, the feed stream is contacted with the catalyst in a reaction zone while maintaining reaction promoting conditions.

The prepared catalysts may be treated so as to improve their stability and activity. "Stabilizing" the catalyst structure means enhancing the resistance of the final catalyst structure to chemical and physical decomposition under the anticipated reaction conditions it will encounter when employed on stream in a hydrocarbon processing reactor operated at reaction temperatures and pressures. Stabilizing preferably includes thermally conditioning the catalyst during catalyst construction, i.e., at intermediate and final stages of catalyst preparation using methods well known in the art. Thermally conditioning includes heat treating the catalyst, or an intermediate stage of the catalyst, according to a defined heating and cooling program. In some embodiments at least one such heat treatment serves to calcine the catalyst or decompose a precursor compound at an intermediate preparation stage of the catalyst. In some embodiments, the catalyst preparation method also includes reducing the catalyst at a predetermined temperature in a reducing atmosphere.

"Enhanced stability" means that the catalyst is more pressure tolerant (to at least 2 atmospheres of operating pressure, and preferably to at least 100 atmospheres), high temperature resistant (up to at least 1,500° C.) and longer lived (reduced coking) for longer periods of time on-stream than typical hydrocarbon processing catalysts. A stability-enhanced catalyst also avoids the common problem of loss of catalyst metal at higher operating temperatures due to catalyst instability and volatilization.

According to the preferred embodiments of the present invention, the catalyst is sulfided using a sulfur-containing material before, during or after use in the hydrocarbon processing step. Sulfiding includes any step in which the catalyst is exposed to a sulfur-containing material and thereby incorporates sulfur into the catalyst. Without limiting the scope of the invention, it is believed that the formation of a metal sulfide at the catalyst surface suppresses the formation of coke and thereby promotes catalyst activity and extends catalyst life. Preferably, the sulfur-containing material is hydrogen sulfide. However, numerous sulfur-containing materials exist and a person of ordinary skill in the art will recognize that such alternatives may also form metal sulfides, promote catalyst activity and extend catalyst life.

Work thus far has demonstrated reduced coking using a sulfided rhodium and/or platinum catalyst in a syngas generation process. However, these examples are not intended to be limiting. A person of ordinary skill will recognize not only that the sulfiding technique applies to other catalytic metals—e.g., nickel and cobalt—but also to other hydrocarbon processing techniques in which catalyst coke formation limits catalyst activity and life—e.g., catalytic oxidative dehydrogenation.

The preferred embodiments of the present invention may be employed in any hydrocarbon processing reaction in which carbon deposition acts to deactivate the catalyst. For ease of presentation and without limiting the scope of the invention, some of the preferred embodiments deal specifically with catalytic partial oxidation processes. The term "catalytic partial oxidation" when used in the context of the present syngas production methods and catalytic activities, in addition to its usual meaning, can also refer to an overall or net catalytic partial oxidation process, in which a hydrocarbon feedstock—e.g., light alkanes preferably comprising mainly methane—and an oxygen feedstock are supplied as reactants and the resulting product stream is predominantly the partial oxidation products CO and $H_2$, rather than containing an appreciable amount of the complete oxidation products $CO_2$ and $H_2O$.

Without limiting the scope of the present invention, specific embodiments of the present invention involving a process for preparation of syngas from a hydrocarbon feedstock will now be discussed. In accordance with certain embodiments of the present invention, a method or process of converting methane or natural gas and $O_2$ to a product gas mixture containing CO and $H_2$, preferably in a molar ratio of about 2:1 $H_2$:CO, is provided. The process comprises mixing a hydrocarbon feedstock and an oxygen containing feedstock to provide a reactant gas mixture feedstock.

The hydrocarbon feedstock for synthesis gas production may be any gaseous hydrocarbon having a low boiling point, such as methane, natural gas, associated gas, or other sources of light hydrocarbons having from 1 to 5 carbon atoms. Natural gas is mostly methane, but it can also contain up to about 25 mole percent ethane, propane, butane and higher hydrocarbons. Preferably, the feed comprises at least about 50 percent by volume methane, more preferably at least 75 percent by volume, and most preferably at least 85 percent by volume methane.

The oxygen-containing feedstock may be pure oxygen gas, or may be air or $O_2$-enriched air. In some embodiments, steam may also be added to produce extra hydrogen and to control the outlet temperature. The ratio of steam to carbon by weight, when steam is added, may preferably range from about 0 to about 1.

The reactant gas mixture may also include incidental or non-reactive species, in lesser amounts than the primary hydrocarbon and oxygen components. Some such species are $H_2$, CO, $N_2$, NOx, $CO_2$, $N_2O$, Ar, $SO_2$ and $H_2S$, as can exist normally in natural gas deposits. Additionally, in some instances, it may be desirable to include nitrogen gas in the reactant gas mixture to act as a diluent. Nitrogen can be present by addition to the reactant gas mixture or can be present because it was not separated from the air that supplies the oxygen gas.

The methane-containing feed and the oxygen containing gas are mixed in such amounts to give a carbon (i.e., carbon in methane) to oxygen (i.e., molecular oxygen) ratio from about 1.5:1 to about 3.3:1, more preferably, from about 1.7:1 to about 2.1:1. The stoichiometric molar ratio of about 2:1 ($CH_4$:$O_2$) is especially desirable in obtaining the ideal partial oxidation reaction products ratio of 2:1 $H_2$:CO for subsequent Fischer-Tropsch processing. In some embodiments, the syngas production method includes preheating the reactant gas mixture to between about 30° C. and about 750° C. before contacting the catalyst.

The reactant gas mixture is fed into a reactor where it comes into contact with a catalytically effective amount of catalyst. Preferably, the catalyst has already been sulfided using a sulfur containing material such as hydrogen sulfide. Alternatively, the catalyst is sulfided during hydrocarbon processing. This sulfiding process can result from the presence of sulfur-containing material in the reactant gas feedstock or through the addition of a sulfur-containing material to the reactant gas feedstock. In yet another embodiment, the sulfiding step can occur after a hydrocarbon processing step but prior to the formation of unacceptably high levels of coke on the catalyst.

Whether the sulfiding step occurs prior to, during, or after the hydrocarbon processing step, the sulfur-containing material may be at any concentration in the gas stream. Preferably, though, the sulfur-containing material is present in the gas stream at a concentration of between about 1 and about 99 volume percent. More preferably, the sulfur-containing material is present in the gas stream at a concentration of between about 25 and about 75 volume percent. Most preferably, the sulfur-containing material is present in the gas stream at a concentration of between about 40 and about 60 weight percent.

Preferably, the catalytic partial oxidization of light hydrocarbons (such as methane, ethane or propane) to synthesis gas, a mixture of CO and $H_2$, employs a very fast contact (i.e., millisecond range)/fast quench (i.e., less than one second) reactor assembly such as those described in the literature. For example, co-owned U.S. Pat. Nos. 6,409,940 and 6,402,898 describe the use of a millisecond contact time reactor for use in the production of synthesis gas by catalytic partial oxidation of methane. The disclosures of these references are hereby incorporated herein by reference.

The sulfiding process may occur in the same reactor or apparatus in which the hydrocarbon processing reaction occurs. Alternatively, the sulfiding process may occur in a different reactor or apparatus than the one in which the hydrocarbon processing reaction occurs.

Reaction productivity is affected by a variety of processing conditions, including temperature, pressure, gas hourly space velocity (GHSV) and catalyst arrangement within the reactor. As used herein, the term "maintaining reaction promoting conditions" refers to regulating these reaction parameters, as well as reactant feedstock composition and catalyst composition in a manner in which the desired hydrocarbon processing reaction is favored.

Hydrocarbon processing techniques typically employ elevated temperatures to achieve reaction promoting conditions. In certain embodiments of the process, the step of maintaining reaction promoting conditions includes preheating the reactant gas mixture at between about 30° C. and about 750° C., more preferably not more than about 525° C. The hydrocarbon processing reaction is preferably operated at temperatures of from about 450° C. to about 2,000° C., more preferably from about 600° C. to about 1,600° C. As used herein, the terms "autothermal" "adiabatic" and "self-sustaining" mean that after initiation of the hydrocarbon processing reaction, no additional or external heat must be supplied to the catalyst in order for the production of reaction products to continue. Under autothermal or self-sustaining reaction conditions, exothermic reactions provide the heat for endothermic reactions, if any. Consequently, under autothermal process conditions, no external heat source is required.

Hydrocarbon processing techniques frequently employ atmospheric or above atmospheric pressures to maintain reaction promoting conditions. In some embodiments, the method includes maintaining the reactant gas mixture at atmospheric or near-atmospheric pressures of approximately 1 atmosphere while contacting the catalyst. Advantageously, certain preferred embodiments of the process are operated at above atmospheric pressure to maintain reaction promoting conditions. In preferred embodiments, the pressure is up to about 32,000 kPa (about 320 atmospheres), more preferably between about 80 and about 10,000 kPa (between about 0.8 and about 100 atmospheres).

The reactant gas mixture may be passed over the catalyst at any of a variety of gas hourly space velocities (GHSV), which is the volume of reactant gas per volume of catalyst per unit time. Although for ease in comparison with prior art systems space velocities at standard conditions have been used to describe the present invention, it is well recognized in the art that residence time is the inverse of space velocity and that the disclosure of high space velocities equates to low residence times on the catalyst. High throughput systems typically employ high GHSV and low catalyst residence times.

The preferred process conditions include maintaining a catalyst residence time of no more than about 200 milliseconds, preferably under 50 milliseconds, more preferably under 20 milliseconds, with 10 milliseconds being highly preferred. This is accomplished by passing the reactant gas mixture over, or through the porous structure of the catalyst system at a gas hourly space velocity of between about 20,000 and about 100,000,000 $hr^{-1}$, preferably between about 100,000 and about 25,000,000 $hr^{-1}$. Under these operating conditions a flow rate of reactant gases is maintained sufficient to ensure a residence time of no more than about 10 milliseconds with respect to each portion of reactant gas in contact with the catalyst system. When referring to a wire gauze catalyst, the contact time may be calculated as the wire diameter divided by the feed gas stream velocity at inlet conditions (i.e., temperature and pressure at the inlet to the reactor). When employing a catalyst monolith or packed bed of divided catalyst, the surface area, depth of the catalyst bed, and gas flow rate (space velocity) are preferably adjusted to ensure the desired short contact time.

The reactant gas mixture passes over the catalyst and the catalytic materials are heated to the point at which they ignite and start the reaction. The product gas mixture emerging from the reactor is harvested and may be routed directly into any of a variety of applications. For example, in the case of syngas generation processes, the CO and $H_2$ product stream may be used for producing higher molecular weight hydrocarbon compounds using Fischer-Tropsch technology. For such processing, the product gas mixture emerging from the reactor preferably has the desired Fischer-Tropsch syngas feed $H_2$:CO ratio of about 2:1. In preferred embodiments of the process, the catalyst system catalyzes the net partial oxidation of at least 90 percent of a methane feedstock to CO and $H_2$ with a selectivity for CO and $H_2$ products of at least about 90 percent CO and 90 percent $H_2$.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, the mixing process can be altered or replaced with an active mixer, the thermal barrier can be modified, the structure and composition of the catalyst can be varied, and the tail gas treatment steps can be modified. Also, it can be readily appreciated that a conventional catalytic partial oxidation process for preparing synthesis gas may be improved to provide better syngas yield and selectivity for CO and $H_2$ products by applying the above-described methods and catalysts and making appropriate additions and modifications of presently available short contact time reactors.

Accordingly, the scope of protection is not limited by the description set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. Use of the term "optionally" with respect to any element of a claim is intended to mean that the subject element is required, or alternatively, is not required. Both alternatives are intended to be within the scope of the claim. The discussion of a reference in the Description of Related Art is not an admission that it is prior art to the present invention, especially any reference that may have a publication date after the priority date of this application. The disclosures of all patents, patent applications and publications cited herein are hereby incorporated herein by reference, to the extent that they provide exemplary, procedural or other details supplementary to those set forth herein.

What is claimed is:

1. A method for reducing coke formation in a catalytic syngas generation process, comprising:
   a) providing a catalytic material effective in catalyzing a catalytic syngas generation reaction;
   b) sulfiding the catalytic material with a sulfur-containing material effective in reducing the susceptibility of the catalytic material to coke formation; and
   c) using the catalytic material in a catalytic syngas generation process.

2. The method of claim 1 wherein the catalytic material is selected from the group consisting of scandium, titanium, vanadium, chromium, manganese, iron, cobalt, nickel, copper, zirconium, niobium, molybdenum, technetium, ruthenium, rhodium, palladium, silver, hafnium, tantalum, tungsten, rhenium, osmium, iridium, platinum, gold, and any combination thereof.

3. The method of claim 1 wherein the catalytic material is selected from the group consisting of platinum, rhodium, ruthenium, iridium, nickel, palladium, iron, cobalt, rhenium, rubidium, or any combination thereof.

4. The method of claim 1 wherein the catalytic material is a mixed-metal catalyst comprising at least one metal selected from the group consisting of rhodium, ruthenium and iridium and at least one other metal selected from the group consisting of platinum and palladium.

5. The method of claim 4 wherein the mixed-metal catalyst is comprised of platinum and rhodium.

6. The method of claim 4 wherein the mixed-metal catalyst includes one or more promoters selected from the group consisting of Mg, B, Al, Ln, Ga, Si, Ti, Zr, Hf, Cr, Mn, Co, Mo, W, Sn, Re, Rh, Pd, Ru, Ir, Pt, La, Ce, Sm, Yb, Eu, Pr, Lu, Bi, Sb, In, P, and their oxides.

7. The method of claim 4 wherein the mixed-metal catalyst is supported on a refractory material selected from the group consisting of silicon carbide, boron carbide, tungsten carbide, silicon nitride, boron nitride, tungsten nitride, zirconia, magnesium-stabilized zirconia, zirconia-stabilized alumina, yttrium-stabilized zirconia, calcium-stabilized zirconia, alumina, cordierite, titania, silica, magnesia, niobia, vanadia, or any combination thereof.

8. The method of claim 4 wherein the mixed-metal catalyst is supported on a refractory material selected from the group consisting of zirconia, alumina, or a combination of the two.

9. The method of claim 7 wherein the refractory material is configured as discrete particles having shapes selected from the group consisting of granules, beads, pills, pellets, cylinders, trilobes, extrudates, spheres, other rounded shapes, and irregularly shaped particles.

10. The method of claim 9 wherein the mixed-metal catalyst is retained in a fixed-bed arrangement.

11. The method of claim 9 wherein the mixed-metal catalyst is retained in a fluidized-bed arrangement.

12. The method of claim 9 wherein the mixed-metal catalyst is retained in an ebulliating-bed arrangement.

13. The method of claim 4 wherein the sulfur-containing material is a sulfur-containing gas.

14. The method of claim 13 wherein the sulfur-containing gas is hydrogen sulfide.

15. The method of claim 1 wherein a feedstock to the catalytic syngas generation process comprises natural gas.

16. The method of claim 1 wherein a feedstock to the catalytic syngas generation process comprises methane.

17. The method of claim 1 wherein a feedstock to the catalytic syngas generation process comprises an oxygen-containing gas.

18. The method of claim 17 wherein the oxygen-containing gas is air or $O_2$-enriched air.

19. The method of claim 17 wherein the oxygen-containing gas is oxygen gas.

20. The method of claim 1 wherein the catalytic syngas generation process is a catalytic oxidative dehydrogenation process.

21. The method of claim 20 wherein a feedstock to the catalytic oxidative dehydrogenation process comprises gaseous and/or liquid paraffins.

22. The method of claim 20 wherein a feedstock to the catalytic oxidative dehydrogenation process comprises ethane.

23. The method of claim 20 wherein a feedstock to the catalytic oxidative dehydrogenation process comprises an oxygen-containing gas.

24. The method of claim 23 wherein the oxygen-containing gas is air or $O_2$-enriched air.

25. The method of claim 23 wherein the oxygen-containing gas is oxygen gas.

26. The method of claim 1 wherein the sulfiding of the catalytic material occurs prior to the use of the catalytic material in the catalytic syngas generation reaction.

27. The method of claim 1 wherein the sulfiding of the catalytic material occurs during the use of the catalytic material in the catalytic syngas generation reaction.

28. The method of claim 1 wherein the sulfiding of the catalytic material occurs following the use of the catalytic material in the catalytic syngas generation reaction.

29. The method of claim 1 wherein the catalytic syngas gereration reaction occurs in a reactor apparatus and the sulfiding of the catalytic material occurs in a different apparatus.

30. The method of claim 1 wherein the catalytic syngas generation reaction occurs in a reactor apparatus and the sulfiding of the catalytic material also occurs in the reactor apparatus.

31. The method of claim 1 wherein the catalytic syngas generation reaction occurs at a temperature between about 600° C. and about 1,600° C.

32. The method of claim 1 wherein the catalytic syngas generation reaction occurs at a pressure between about 80 kPa and about 10,000 kPa.

33. The method of claim 1 wherein the catalytic syngas generation reaction occurs at a space velocity between about 20,000 $hr^{-1}$ and about 100,000,000 $hr^{-1}$.

34. The method of claim 1 wherein the catalytic syngas generation reaction occurs at a temperature between about 600° C. and about 1,600° C., at a pressure between about 80 kPa and about 10,000 kPa, and at a space velocity between about 20,000 $hr^{-1}$ and about 100,000,000 $hr^{-1}$.

35. The method of claim 1 wherein the catalytic material is selected from the group consisting of platinum, rhodium, or a combination of the two.

36. The method of claim 3 wherein the catalytic material includes one or more promoters selected from the group consisting of Mg, B, Al, Ln, Ga, Si, Ti, Zr, Hf, Cr, Mn, Co, Mo, W, Sn, Re, Rh, Pd, Ru, Ir, Pt, La, Ce, Sm, Yb, Eu, Pr, Lu, Bi, Sb, In, P, and their oxides.

37. The method of claim 3 wherein the catalytic material is supported on a refractory material selected from the group consisting of silicon carbide, boron carbide, tungsten carbide, silicon nitride, boron nitride, tungsten nitride, zirconia, magnesium-stabilized zirconia, zirconia-stabilized alumina, yttrium-stabilized zirconia, calcium-stabilized zirconia, alumina, cordierite, titania, silica, magnesia, niobia, vanadia, or any combination thereof.

38. The method of claim 3 wherein the catalytic material is supported on a refractory material selected from the group consisting of zirconia, alumina, and a combination of the two.

39. The method of claim 37 wherein the refractory material is configured as discrete particles having shapes selected from the group consisting of granules, beads, pills, pellets, cylinders, trilobes, extrudates, spheres, other rounded shapes, and irregularly shaped particles.

40. The method of claim 39 wherein the catalytic material is retained in a fixed-bed arrangement.

41. The method of claim 39 wherein the catalytic material is retained in a fluidized-bed arrangement.

42. The method of claim 39 wherein the catalytic material is retained in an ebulliating-bed arrangement.

43. The method of claim 1 wherein the sulfur-containing material is a sulfur-containing gas.

44. The method of claim 43 wherein the sulfur-containing gas is hydrogen sulfide.

* * * * *